USO10368813B2

United States Patent
Sato et al.

(10) Patent No.: US 10,368,813 B2
(45) Date of Patent: Aug. 6, 2019

(54) PHOTOACOUSTIC APPARATUS AND METHOD WITH USER SELECTABLE DIRECTIVITY ANGLES FOR DETECTION

(71) Applicant: CANON KABUSHIKI KAISHA, Tokyo (JP)

(72) Inventors: Akira Sato, Kawasaki (JP); Minoru Ohkoba, Sagamihara (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 660 days.

(21) Appl. No.: 14/748,349

(22) Filed: Jun. 24, 2015

(65) Prior Publication Data

US 2015/0374312 A1    Dec. 31, 2015

(30) Foreign Application Priority Data

Jun. 26, 2014    (JP) .................................. 2014-131663

(51) Int. Cl.
*A61B 5/00*    (2006.01)
*G01N 21/17*    (2006.01)

(52) U.S. Cl.
CPC .......... *A61B 5/7475* (2013.01); *A61B 5/0062* (2013.01); *A61B 5/0091* (2013.01); *A61B 5/0095* (2013.01); *A61B 5/4312* (2013.01); *A61B 5/748* (2013.01); *G01N 21/1702* (2013.01); *A61B 5/708* (2013.01);
(Continued)

(58) Field of Classification Search
None
See application file for complete search history.

(56) References Cited

U.S. PATENT DOCUMENTS 5,713,356 A * 2/1998 Kruger ................. A61B 5/0091
600/407
5,902,241 A * 5/1999 Seyed-Bolorforosh ......................
G01S 7/52046
600/443
(Continued)

FOREIGN PATENT DOCUMENTS

JP    2007-508043 A    4/2007
JP    2012-179348 A    9/2012
(Continued)

OTHER PUBLICATIONS

European Extended Search Report dated Dec. 3, 2015 in counterpart European patent application 15173784.8 (in English).
(Continued)

*Primary Examiner* — James M Kish
(74) *Attorney, Agent, or Firm* — Venable LLP

(57) ABSTRACT

To use an object information acquiring apparatus that has: a plurality of detection elements that detect acoustic waves generated from an object irradiated with light from a light source and output electric signals; a supporting member that supports the plurality of detection elements so that the axes of directivity of at least part of the detection elements gather; an inputting unit that receives an input of a measurement condition from a user; a selecting unit that selects at least part of the plurality of detection elements in response to the measurement condition input by the user; and a processing unit that acquires property information on the inside of the object, using electric signals output from the selected detection elements.

21 Claims, 6 Drawing Sheets

(52) U.S. Cl.
CPC ........... *A61B 5/742* (2013.01); *A61B 2576/00* (2013.01); *G01N 2021/1706* (2013.01); *G01N 2201/067* (2013.01)

(56) References Cited

U.S. PATENT DOCUMENTS

| | | | |
|---|---|---|---|
| 6,459,925 B1* | 10/2002 | Nields | A61B 6/0435 |
| | | | 128/915 |
| 6,866,632 B1* | 3/2005 | Chou | G01S 7/52047 |
| | | | 128/916 |
| 9,766,211 B2 | 9/2017 | Oishi | |
| 2006/0058670 A1* | 3/2006 | Lin | G03B 42/06 |
| | | | 600/447 |
| 2007/0123110 A1 | 5/2007 | Schwartz | |
| 2012/0095343 A1* | 4/2012 | Smith | A61B 8/4483 |
| | | | 600/447 |
| 2013/0312526 A1 | 11/2013 | Oishi | |
| 2017/0350869 A1 | 12/2017 | Oishi | |

FOREIGN PATENT DOCUMENTS

| | | |
|---|---|---|
| WO | WO 2009/031079 A | 3/2009 |
| WO | WO 2013/082586 A | 6/2013 |

OTHER PUBLICATIONS

U.S. Appl. No. 14/736,381, filed Jun. 11, 2015.
U.S. Appl. No. 14/737,753, filed Jun. 12, 2015.
U.S. Appl. No. 14/751,330, filed Jun. 26, 2015.
Office Action dated Apr. 3, 2018, in counterpart application JP 2014-131663 (9 pages).

* cited by examiner

PHOTOACOUSTIC APPARATUS AND METHOD WITH USER SELECTABLE DIRECTIVITY ANGLES FOR DETECTION

BACKGROUND OF THE INVENTION

Field of the Invention

The present invention relates to an object information acquiring apparatus and an object information acquiring method.

Description of the Related Art

A photoacoustic imaging (PAI) method has been proposed as a technique for imaging the inside of an object using acoustic waves (typically, ultrasonic waves). The photoacoustic imaging method is a method for visualizing information related to the optical property values inside an object by using acoustic waves generated by irradiating the object with pulsed laser light.

U.S. Pat. No. 5,713,356 discloses a method for receiving acoustic waves from an object (a breast) by using a plurality of transducers arranged on a hemispherical surface of a detector and generating (reconstructing) three-dimensional image data. Upon measurement using this apparatus, one inserts her breast into the hemispherical detector in which the transducers are arranged, and lies on her stomach. A gap between the inserted breast and the transducers is filled with water for acoustic matching. At the time of measurement, the detector provided with the transducers rotates step by step. Consequently, the transducers receive acoustic waves at each step position. The detector scans the breast in this manner, so that it is possible to perform measurement as if transducers were present in many directions, even when a small number of transducers are used. Note that the breast is inserted to be located in the vicinity of the center of the hemisphere of the detector, and pulsed light is emitted from the top portion of the hemisphere of the detector.
Patent Literature 1: U.S. Pat. No. 5,713,356

SUMMARY OF THE INVENTION

In a case where a plurality of transducers are arranged on a hemispherical surface as in U.S. Pat. No. 5,713,356, a region of high sensitivity is present due to the element properties (e.g., sensitivity, directivity, etc.) of each transducer and the positional relationship between the transducers. This region is called "high-resolution region," in the present specification. The size and resolution of the high-resolution region are generally determined uniquely depending on the design of the apparatus. In U.S. Pat. No. 5,713,356, the properties such as the size and resolution of the high-resolution region are constant.

However, measurement using the constant high-resolution region as described in U.S. Pat. No. 5,713,356 has difficulty addressing user needs for resolution in measurement.

The present invention was contrived in view of the foregoing problem. An object of the present invention is to address the user needs for resolution in measurement in photoacoustic imaging.

The present invention provides an object information acquiring apparatus, comprising:
a light source;
a plurality of detection elements configured to detect acoustic waves generated as a result of irradiation of light from the light source onto an object and to output electric signals;
a supporting member configured to support the plurality of detection elements so that axes of directivity of at least a part of the plurality of detection elements gather;
an inputting unit configured to receive an input of a measurement condition from a user;
a selecting unit configured to select at least a part of the plurality of detection elements in response to the measurement condition input by the user; and
a processing unit configured to acquire property information on the inside of the object, using electric signals output from the detection elements selected by the selecting unit.

The present invention also provides an object information acquiring method, comprising:
a first step of determining a measurement condition;
a second step of selecting, in accordance with the measurement condition determined in the first step, at least a part of a plurality of detection elements configured to output electric signals corresponding to acoustic waves generated as a result of irradiation of light onto an object, and disposed in a manner that axes of directivity gather; and
a third step of acquiring property information on the inside of the object by using the electric signals output from the detection elements selected in the second step.

According to the present invention, the user needs for resolution in measurement can be addressed in photoacoustic imaging.

Further features of the present invention will become apparent from the following description of exemplary embodiments with reference to the attached drawings.

DESCRIPTION OF THE EMBODIMENTS

Figure 1:
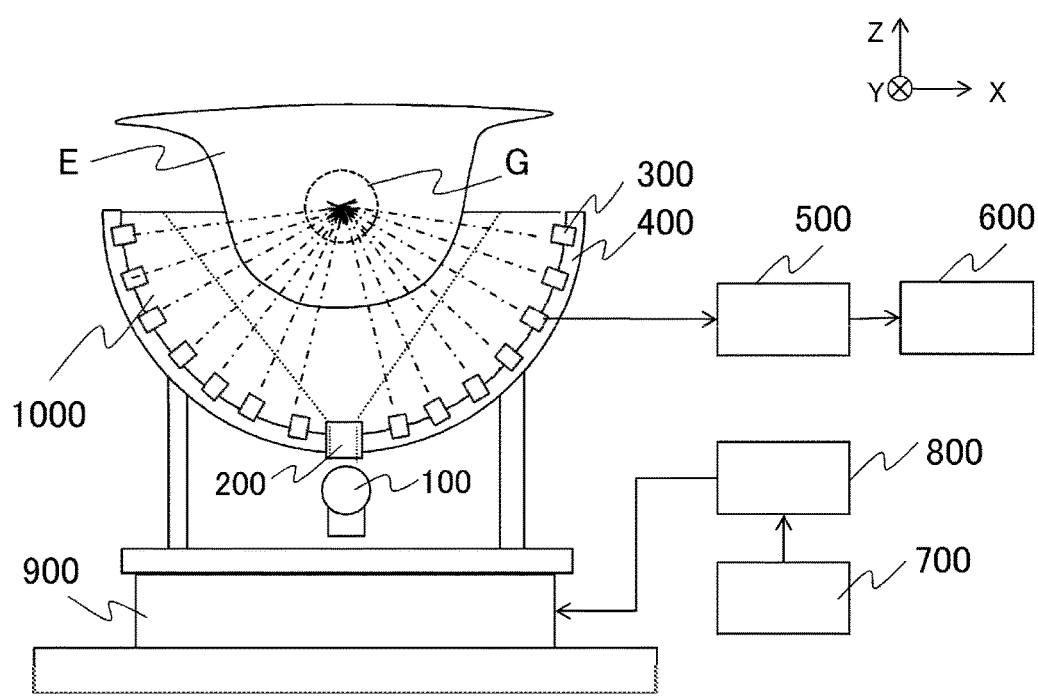
FIG. 1 is a block diagram showing a configuration of an apparatus according to Embodiment 1.

Preferred embodiments of the present invention are now described hereinafter with reference to the drawings. The sizes, materials, shapes, relative arrangements, and the like of the components described hereinafter are not intended to limit the scope of the present invention to the following descriptions but may be changed based on the configurations of the apparatus and various conditions to which the present invention is applied.

The present invention may be used when detecting acoustic waves propagating from an object and generating and imaging property information of the inside of the object. Therefore, the present invention may be considered as an object information acquiring apparatus and a control method thereof, an object information acquiring method, and a signal processing method. The present invention may also be considered as a program for causing an information processing apparatus with hardware resources such as a CPU to execute these methods, and a non-temporary storage medium for storing this program.

An object information acquiring apparatus of the present invention includes an apparatus that uses a photoacoustic effect of receiving acoustic waves generated inside an object by irradiating the object with light (electromagnetic waves) and acquiring the object information as image data. In case of this photoacoustic apparatus, the object information to be acquired represents a distribution of the sources of the acoustic waves generated by light irradiation, an initial acoustic pressure distribution in the object, a light energy absorption density distribution derived from the initial acoustic pressure distribution, an absorption coefficient distribution, or a density distribution of the substances configuring the tissues. Examples of the density distribution of the substances include a distribution of degrees of oxygen saturation, and an oxygenated/reduced hemoglobin density distribution.

Displaying such information in the form of image data allows a user to understand the structure inside the object. Ultrasonic waves described in the present invention include sound waves and elastic waves called acoustic waves. Electric signals that are obtained by converting acoustic waves using probes (or elements within the probes) are called "acoustic signals."

There are various user needs, such as wishing to measure a wide region at low resolution within a short period of time and wishing to measure a narrow region at high resolution. However, the conventional apparatuses basically cannot change the sizes or sensitivity properties of high-resolution regions, and therefore cannot accommodate such needs. Specifically, for example, even when the user wishes to measure a wide region at low resolution, it takes a long time to scan the set region with a small high-resolution region (by gradually moving the high-resolution region). Alternatively, even when the set region is smaller than the high-resolution region, the measurement is performed with the uniform high-resolution region, requiring extra time.

Embodiment 1

FIG. 1 is a schematic diagram showing a configuration of a photoacoustic apparatus according to a preferred embodiment of the present invention. The photoacoustic apparatus shown in FIG. 1 acquires property information of an object E (e.g., a breast) to generate image data of the inside of the object E.

The photoacoustic apparatus according to the present embodiment has a light source 100, an optical system 200 functioning as a light irradiation unit, acoustic detection elements 300, a supporting member 400, an element selecting unit 500, a signal processing unit 600, an inputting unit 700, a scanning region setting unit 800, a scanner 900, and an acoustic matching material 1000.

The object and these configurations are described hereinafter.

(Object)

The object E is a target of measurement. Specific examples of the object E include a living tissue such as a breast, and a phantom simulating the acoustic property information and optical properties of the organism for adjustments of the apparatus. The acoustic properties are, specifically, the propagation velocities and attenuations of acoustic waves, whereas the optical properties are, specifically, optical absorption coefficients and scattering coefficients. A light absorber of high optical absorption coefficient needs to be present in the object. In case of an organism, hemoglobin, water, melanin, collagen, fat and the like are the light absorbers. In case of a phantom, a material simulating the optical properties is enclosed in the phantom as a light absorber.

(Light Source)

The light source 100 is a device that generates pulsed light. For the purpose of obtaining a large output power, laser is desired as the light source, but a light-emitting diode can also be used in place of laser. In order to generate photoacoustic waves effectively, light needs to be radiated within a sufficiently short period of time in accordance with the thermal properties of the object. In a case where the object is an organism, the pulse width of pulsed light generated by the light source 100 is desired to be equal to or less than several tens of nanoseconds. Also, the wavelength of the pulsed light is desired to be equivalent to a near infrared region called "biological window," which is approximately 700 nm to 1200 nm. Light in this region can reach relatively deep in the organism, and is therefore favorable in acquiring the information of the deep portion of the organism. If the measurement is limited to a surface portion of the organism, visible light of approximately 500 nm to 700 nm to a near infrared radiation may be used as well. Moreover, the wavelength of the pulsed light is desired to have a high absorption coefficient with respect to the object to be observed.

(Optical System)

The optical system 200 is a device for guiding the pulsed light generated by the light source 100 to the object E. Specifically, the optical system 200 can be an optical device such as a lens, a mirror, a prism, optical fibers, or a diffuser panel, or a combination thereof. When guiding the light, sometimes these optical devices are used to change the shape and optical density of the light to obtain a desired optical distribution. Not only these optical devices, but also any optical devices that satisfy such functions may be used. The optical device corresponds to the irradiation unit of the present invention.

The intensity of the light that can be radiated onto the tissues of the organism is defined by a maximum permissible exposure (MPE) based on a predetermined safety standard. Examples of the safety standard include IEC 60825-1: Safety of laser products, JIS C 6802: Safety Standards for Laser Products, FDA: 21CFR Part 1040.10, ANSI Z136.1: Laser Safety Standards, and the like. The maximum permissible exposure defines the intensity of the light that can be radiated per unit area. In order to obtain a favorable internal image of the object while keeping the maximum permissible exposure, it is preferred that the light be radiated at once onto a wide region on the surface of the object E. This allows a large amount of light to be guided to the object E while controlling the optical intensity per unit area, enabling reception of a photoacoustic wave at a high SN ratio. Therefore, instead of focusing the light with a lens, it is preferred to have a somewhat large region, as shown by the broken lines extending from the optical system 200 in FIG. 1.

(Acoustic Detection Elements)

The acoustic detection elements 300 each receive a photoacoustic wave and convert the photoacoustic wave into an electric signal. The acoustic detection elements 300 are desired to have high receiver sensitivity and a wide frequency bandwidth with respect to the photoacoustic waves from the object E. The acoustic detection elements 300 can be configured by a piezoelectric ceramic material such as lead zirconate titanate (PZT), a polymer piezoelectric film material such as polyvinylidene fluoride (PVDF), and the like. Elements other than a piezoelectric element may be used. For example, capacitance type elements such as capacitive micro-machined ultrasonic transducers (cMUTs), acoustic detection elements using Fabry-Perot interferometers and the like can be used.

The acoustic detection elements 300 each have an axial direction having high receiver sensitivity and form a receiving region for receiving a photoacoustic wave in the axial direction at high sensitivity. In the following description, such expression as "the axial direction having high receiver sensitivity" is described as "axis of directivity."

Figure 2A:
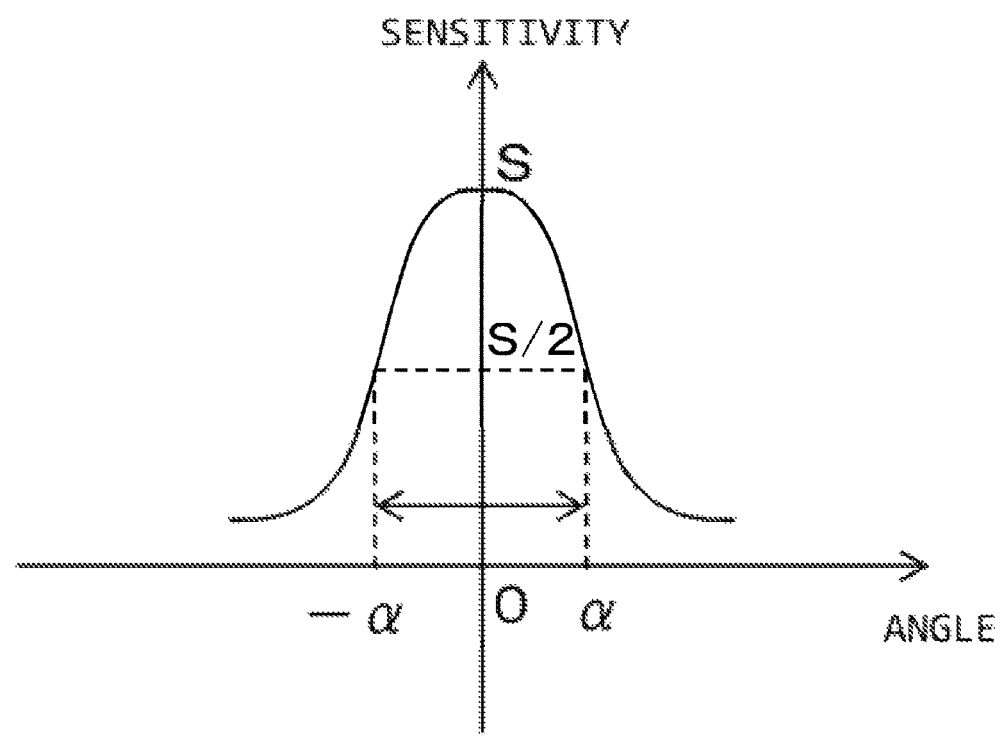
FIGS. 2A and 2B are diagrams showing the sensitivity properties of an acoustic detection element according to Embodiment 1.
Figure 2B:
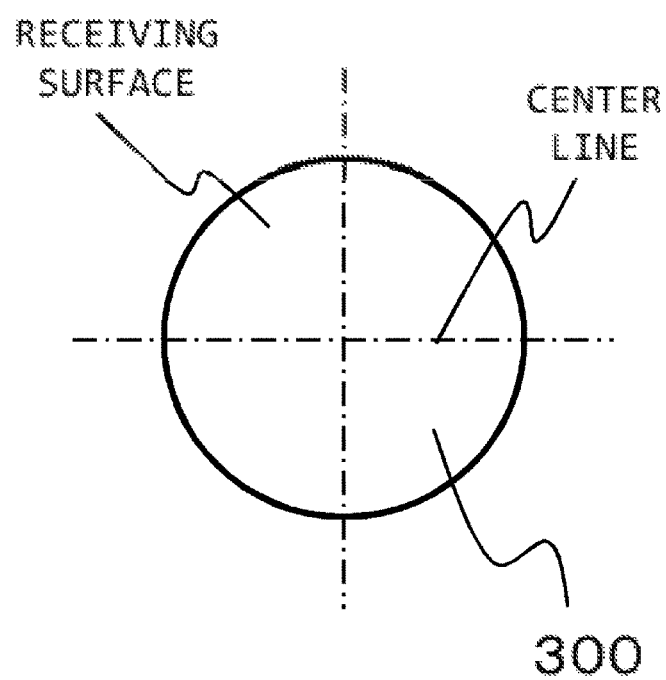

FIG. 2A shows an example of sensitivity properties of each acoustic detection element 300. As shown in FIG. 2B, the acoustic detection element 300 typically has a circular, planar receiving surface. FIG. 2A shows the sensitivity properties corresponding to an incidence angle of 0 degrees at which a photoacoustic wave enters from the normal direction of the receiving surface, the sensitivity properties being taken along a cross section passing through the center line of the acoustic detection element 300 shown in FIG. 2B. In the example shown in FIG. 2A, the sensitivity is the highest when the wave enters from the normal direction of the receiving surface, and the larger the incidence angle, the lower the sensitivity.

Suppose that the incidence angle is α when the sensitivity is half its maximum S, that is, when the sensitivity is S/2. In the present embodiment, this incidence angle α is described as "directivity angle." Furthermore, a region on the receiving surface of the acoustic detection element where the photoacoustic wave enters at an incidence angle equal to or less than α is a region where the photoacoustic wave can be received at high sensitivity. In the following description, the region where the acoustic detection element can receive a photoacoustic wave at high sensitivity is described as "high-sensitivity receiving region."

Therefore, the acoustic detection element 300 has a axis of directivity and a high-sensitivity receiving region around the axis of directivity to receive a photoacoustic wave at high sensitivity. Note that the angle α may be set based not only on a half width of the maximum sensitivity but also on various conditions.

In the present embodiment, each of the acoustic detection elements has two types of directivity properties, the directivity angles of which are α1 and α2 (α1>α2). The acoustic detection elements with the directivity angle α1 are acoustic detection elements 301. The acoustic detection elements with the directivity angle α2 are acoustic detection elements 302. Regardless of the difference between the directivity angles, the entire acoustic detection elements are generically described as "acoustic detection element 300," unless otherwise specified. With regard to the directivity angles of the acoustic detection elements, the elements with a wider opening have a narrower directivity angle. Therefore, the elements with different directivity angles can be prepared by changing the openings. In addition, the elements with different directivity angles can be prepared by forming the receiving surfaces of the elements into concave or convex surfaces or by using acoustic lenses.

(Supporting Member)

The supporting member 400 shown in FIG. 1 is a container in substantially a hemispherical shape, in which the plurality of acoustic detection elements 300 are installed on the inner surface of the hemisphere and the optical system 200 in the lower portion (polar) of the hemisphere. The inside of the hemisphere is filled with solution forming the acoustic matching material 1000 which is described hereinafter. Each of the acoustic detection elements 300 is connected to the signal processing unit 600, described hereinafter, by a lead wire which is not shown. The shape of the supporting member 400 does not have to be a hemispherical shape but may be in the shape of a spherical crown, an ellipsoid whose partial area removed, or a combination of a plurality of flat or curved surfaces. As will be described hereinafter, the supporting member may be formed in any shape to support the plurality of acoustic detection elements, so as to be able to gather the axes of directivity of at least some of the plurality of acoustic detection elements.

Gathering the axes of directivity of two detection elements means that there exists a region where the distance between the axes of directivity is shorter than the distance between the two detection elements. For instance, in a case where the axes of directivity of the two detection elements is parallel to each other, the two axes of directivity do not gather because the distance therebetween do not become shorter than the distance between the detection elements.

It is preferred that the supporting member 400 be configured using a metallic material of high mechanical strength in order to be able to support these members. It is also preferred that the supporting member 400 be provided with a sealing member for preventing the acoustic matching material 1000 from leaking out of the supporting member 400. A member for holding the object E may also be provided on the supporting member 400. The holding member is preferably in the shape of a cup or a bowl and is desired to be transmissive to light from the irradiation unit or a photoacoustic wave from the inside of the object.

When arranging the elements into an array on the hemispherical surface of the supporting member 400, the elements are so arranged that the axes of directivity of at least some of the plurality of acoustic detection elements 300 form angles different from the angles formed by the other axes of directivity. The axes of directivity of the elements intersect with one another at a region located at substantially the center of the hemisphere. FIG. 1 is a cross-sectional diagram taken along the central axis of the hemisphere, in which the dashed lines that gather in a partial region of the object E represent the axes of directivity of the acoustic detection elements 300. The optical system 200 is disposed to irradiate substantially the central region of the hemisphere. In this arrangement, an image obtained by a universal back projection method has a high resolution at the center of the hemisphere and a low resolution away from the center.

In the present embodiment, the acoustic detection elements 301, 302 of two directivities are mounted, in which the acoustic detection elements 301, 302 are disposed adjacent to each other as a pair in each of the acoustic detection elements 300 arranged in a manner described above.

The positional information of each acoustic detection element 300 in the supporting member 400 and of the optical system 200 are stored in a recording device such as a memory, not shown, and are used when generating an image.

In the present specification, a region of high resolution is referred to as "high-resolution region." In the present embodiment, the high-resolution region represents a region between the point of the highest resolution and the point of resolution half the highest resolution. Region G shown in FIG. 1 corresponds to this region. As long as the directions of high reception sensitivities can be directed to a specific region to form the high-resolution region where the property information can be acquired at a predetermined resolution or higher, the directions of the highest sensitivities of the acoustic detection elements do not have to intersect with each other. Moreover, at least some of the plurality of acoustic detection elements supported by the supporting member may be directed to a specific region.

Figure 3A:
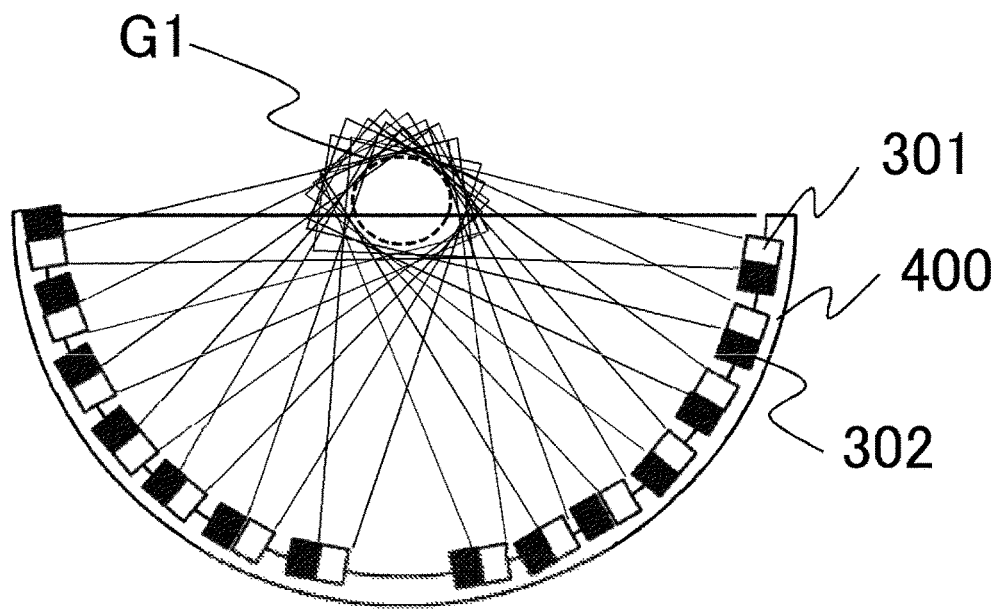
FIGS. 3A and 3B are explanatory diagrams of high-resolution regions according to Embodiment 1.
Figure 3B:
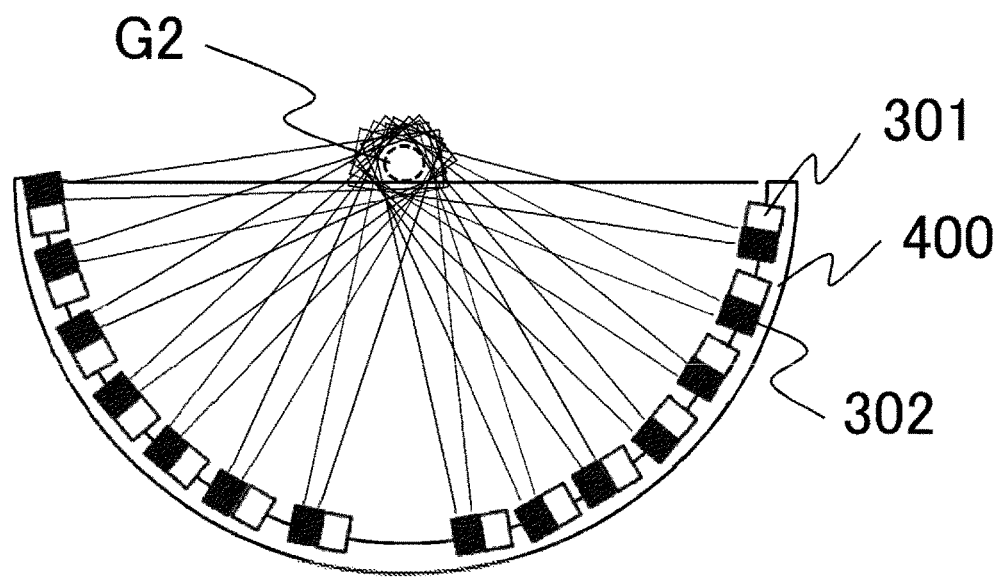

FIG. 3A shows a high-sensitivity receiving region formed only by the acoustic detection elements 301, and FIG. 3B shows a high-sensitivity receiving region formed only by the acoustic detection elements 302. The white acoustic detection elements shown in FIGS. 3A and 3B are the acoustic detection elements 301 having the wide directivity angle α1 (wide directivity angle), and the black acoustic detection elements in the diagrams are the acoustic detection elements 302 having the narrow directivity angle α2 (narrow directivity angle). The acoustic detection elements 301 and 302 are disposed adjacent to each other and are attached so that the axes thereof are directed to the same region. The lines extending radially from the acoustic detection elements represent the ranges within the directivity angles of the elements. When each of the elements detects an acoustic wave, a signal corresponding to the range of the radial lines is obtained. Dotted line regions G1 and G2 within the regions where the radial lines come together are the high-resolution regions.

Here, the high-resolution region G1, which is formed when using a group of acoustic detection elements 301 having the wide directivity angle, is wider than a region, which is formed when using a group of acoustic detection elements 302 having the narrow directivity angle. As described above the acoustic detection elements having the wider the directivity angle tend to exhibit lower the sensitivity. Therefore, although the high-resolution region G1 in FIG. 3A is wide, the sensitivity there of is low sensitivity, whereas although the high-resolution region G2 shown in FIG. 3B is narrow, the sensitivity there of is high.

Scanning the supporting member 400 can expand the high-resolution region inside the object.

(Element Selecting Unit)

The element selecting unit 500 shown in FIG. 1 is a unit for selecting an acoustic detection element to be actually used from among the acoustic detection elements 300. Based on an imaging instruction from the user, the element selecting unit 500 serves to select an acoustic detection element to be actually used and connect the acoustic detection element to be used to the signal processing unit. Specific methods for selecting an acoustic detection element to be used are described hereinafter. One possible configuration in implementing the selecting unit 500 is as a programmed CPU.

In the present embodiment, the selecting unit is configured with a switch portion for connecting the acoustic detection element to be used to the signal processing unit. However, a switch for switching the circuit connection and the element selecting unit 500 may be configured as separate devices. The element selecting unit corresponds to the selecting unit of the present invention.

(Signal Processing Unit)

The signal processing unit 600 functions to store the electric signals that are input from the acoustic detection elements 300. The signal processing unit 600 also functions to generate the property information such as the optical properties of the inside of the object E by using the electric signals that are input from the acoustic detection elements 300, and generate an image of the inside of the object E based on the property information. The signal processing unit 600 also functions to execute processes for operating the photoacoustic apparatus, such as controlling the light emission of the light source 100 and driving the scanner 900. The signal processing unit corresponds to the processing unit of the present invention.

An arithmetic unit of the signal processing unit 600 is typically configured with an element such as a CPU, a GPU, or an A/D converter or a circuit such as an FPGA or an ASIC. The arithmetic unit may be configured not only with a single element or circuit but also with a plurality of elements or circuits. The processes executed by the signal processing unit 600 may be executed by any of the elements or circuits.

A storage unit of the signal processing unit 600 is typically configured with a storage medium such as a ROM, a RAM, or a hard disk. The storage unit may be configured not only with a single storage medium but also with a plurality of storage media.

It is preferred that the signal processing unit 600 be configured to be able to pipeline a plurality of signals at the same time, so that the amount of time it takes to acquire the information on the object can be reduced.

The processes executed by the signal processing unit 600 can be stored in the storage unit as programs to be executed by the arithmetic unit. However, the storage unit in which the programs are stored is a non-temporary recording medium. The signal processing unit, the element selecting unit, a scanning control unit and the like may each be configured with a circuit or an information processing apparatus or as a functional block of a single information processing apparatus.

(Inputting Unit)

The inputting unit 700 is input means used by the user to input a measurement instruction. In the present embodiment, the inputting unit 700 can input an instruction for designating a three-dimensional region of interest and performing advanced settings for realizing measurement. The user designates the region of interest with reference to a captured image of the object E that is displayed by a display unit, not shown. The captured image of the object E is an image captured by a capture camera, not shown. When performing the advanced settings for realizing measurement, measurement conditions can be selected in the present embodiment. The details of selecting the measurement conditions are described hereinafter. In the present embodiment, an element to be used for measurement is determined by selecting the measurement conditions. In addition, in order to execute input for the same purpose, a method for selecting an element to be used or inputting the designations of the shapes and sizes of the high-resolution regions may be used.

An interface of the inputting unit may be a pointing device such as a mouse or a keyboard, a pen tablet, or a touchpad attached to the front surface of the display unit, not shown. The display unit may be configured as a touch panel.

(Scanning Region Setting Unit)

The scanning region setting unit 800 is a device for setting scanning regions in X, Y and Z directions in which the supporting member 400 is moved. The scanning region setting unit 800 establishes X, Y, Z regions for moving the supporting member 400, in such a manner as to include a three-dimensional region of interest, designated using the inputting unit 700, within the trajectory range of the high-resolution region G that is formed by scanning the supporting member 400 in the X, Y and Z directions. The present embodiment employs a method for calculating a Z-coordinate position containing the region of interest and then scanning an XY plane in a spiral manner. In so doing, a scan trajectory is scheduled based on the shape (size) of the high-resolution region defined by a combination of acoustic detection elements selected by the selecting unit. Scheduling the scan trajectory is described hereinafter in detail.

(Scanner)

The scanner 900 is a device for changing the position of the supporting member 400 in relation to the object E by scanning the position of the supporting member 400 in the X, Y and Z directions shown in FIG. 1. Therefore, the scanner 900 has a guide mechanism for the X, Y and Z directions, not shown, a drive mechanism for the X, Y and Z directions, and a position sensor for detecting the X-, Y- and Z-direction positions of the supporting member 400. As shown in FIG. 1, since the supporting member 400 is placed on the scanner 900, it is preferred that a linear guide or the like that can withstand large load be employed as the guide mechanism. A lead screw mechanism, a link mechanism, a gear mechanism, a hydraulic mechanism or the like can be used as the drive mechanism. A motor or the like can be used as the driving power. A potentiometer using an encoder, a variable resistor or the like can be used as the position sensor. The scanner corresponds to the scanning unit of the present invention.

(Acoustic Matching Material)

The acoustic matching material 1000 acoustically bonds the object E and the acoustic detection elements 300 by filling the space between the object E and the acoustic detection elements 300. The material thereof is desired to be fluid that has an acoustic impedance similar to those of the object E and the acoustic detection elements 300 and allows penetration of the pulsed light generated by the light source 100. Specifically, water, castor oil, gel or the like can be used.

Figure 6:
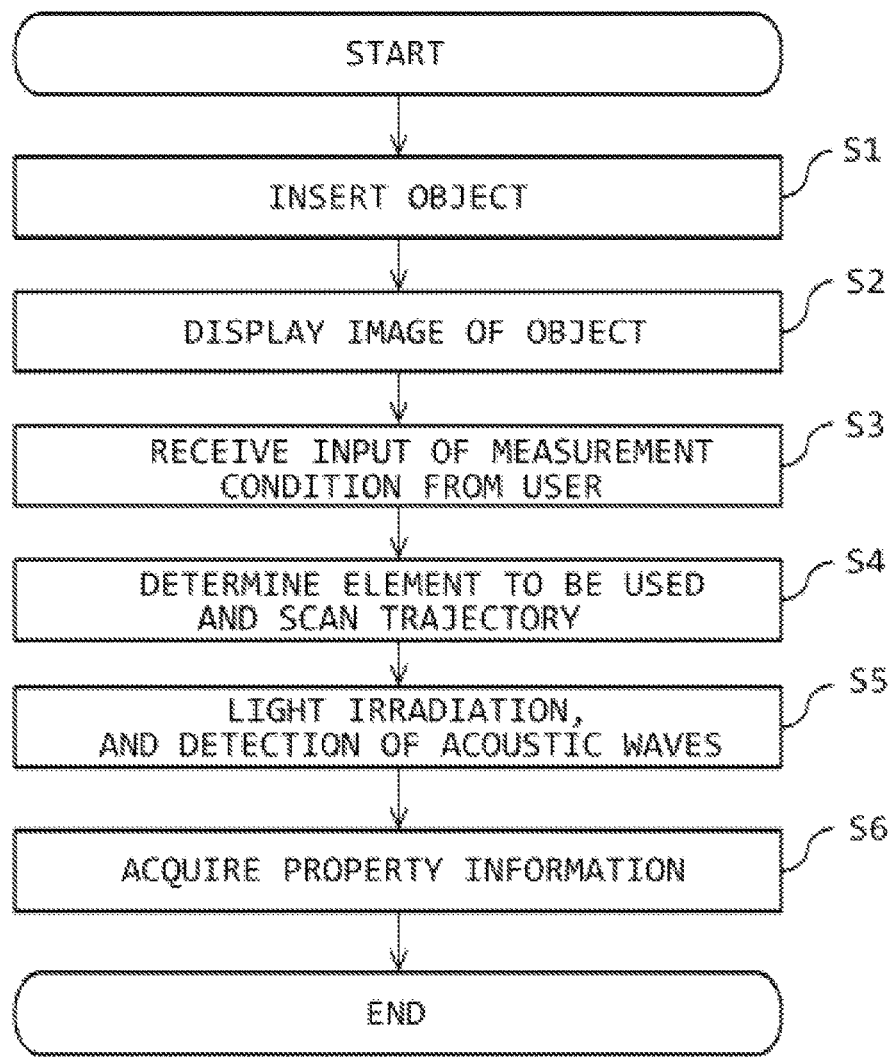
FIG. 6 is a flowchart for explaining a process according to Embodiment 1.

Next are described some of the properties of the present invention, which are the steps of determining an acoustic detection element to be used and a method for acquiring a photoacoustic wave which is executed based on the determined acoustic detection element. If necessary, the step numbers of the flowchart shown in FIG. 6 are described as well.

First, the object is inserted into the apparatus (step S1). Consequently, a captured image of the object is displayed by the display unit, as described above (step S2). The user sees the image and inputs a measurement instruction using the inputting unit 700. When inputting the measurement instruction, the measurement conditions such as a three-dimensional region of interest, a measurement wavelength, and a measurement method are set (step S3).

When selecting measurement conditions, two types of scan modes, i.e., quick scan and detailed scan, can be designated as the measurement method. The quick scan is a scan mode for performing scanning within a short period of time with the lowered the resolution. The detailed scan is performed with the high resolution. Being able to select the time it takes for measurement is important for the purpose of lowering the burdens on the subject person.

The measurement instruction that is set using the inputting unit 700 is sent to the element selecting unit 500, whereby an element to be used is determined as follows (step S4).

(Method for Selecting Element to be Used)

In the present embodiment, the acoustic detection elements 300 have a group of acoustic detection elements 301 with the wide directivity angle and a group of acoustic detection elements 302 with the narrow directivity angle. These elements can be referred to as a first pattern, which is a combination of the elements having the wide directivity angle, and a second pattern, which is a combination of the elements having the narrow directivity angle. The terms "wide directivity angle" and "narrow directivity angle" are not intended to define specific angles but to compare the first pattern, which is a combination of the elements having a predetermined directivity angle, with the second pattern, which is a combination of the elements having a directivity angle narrower than the predetermined angle. The elements configuring the first pattern correspond to the first detection elements of the present invention, while the elements configuring the second pattern correspond to the second detection elements of the present invention.

The element selecting unit 500 determines which one of the two groups (patterns) to use. Specifically, after the measurement instruction is input, the element selecting unit 500 refers to the measurement types. When the measurement type is the quick scan mode, the element selecting unit 500 selects the group of acoustic detection elements 301 having the wide directivity angle. When the measurement type is the detailed scan mode, the element selecting unit 500 selects the group of acoustic detection elements 302 having the narrow directivity angle. The element selecting unit 500 switches the wiring so that the selected group of elements is bonded to the signal processing unit 600 in the form of a circuit. In the quick scan, the distance the supporting member 400 moves between light irradiations is greater compared to the detailed scan. In other words, in the detailed scan, a pitch between the positions to which the supporting member 400 is moved in each light irradiation is smaller than that obtained in the quick scan. According to the scanning method and measurement conditions, the quick scan can be referred to as "first measurement condition" under which the pitch is a relatively large predetermined value, and the detailed scan can be referred to as "second measurement condition" under which the pitch is smaller than the predetermined value. In other words, the element selecting unit 500 selects the first detection elements or the second detection elements depending on the measurement conditions.

Next, the scanning region setting unit 800 executes scheduling of the scan trajectory.

(Scan Trajectory Scheduling)

With reference to the information on the group of elements determined by the element selecting unit 500, the scanning region setting unit 800 calculates the size of the high-resolution region formed by this combination of the information. Based on the calculated size of the high-resolution region, a radial pitch of a spiral trajectory (spiral pitch) and photoacoustic measurement positions in scanning can be determined. In addition, the number of windings in spiral scan can be determined based on the three-dimensional region of interest that is set by the user.

The relationship between the scan trajectory scanning and the three-dimensional region of interest and high-resolution region is described with reference to FIG. 4.

Figure 4A:
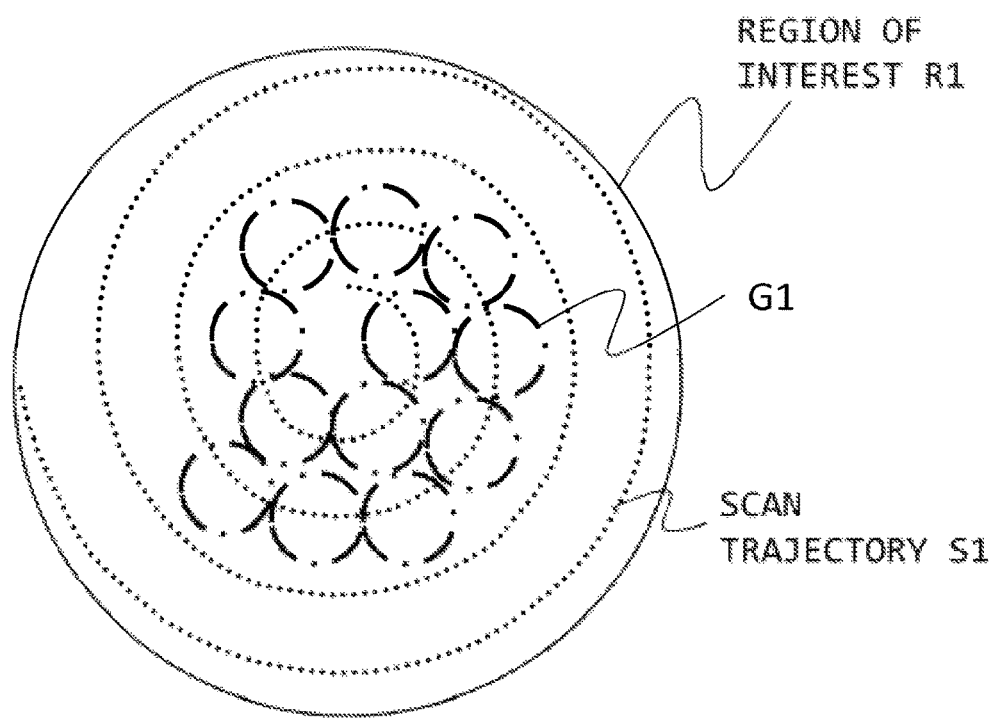
FIGS. 4A and 4B are explanatory diagrams of a scan trajectory of each high-resolution region according to Embodiment 1.

FIG. 4A shows how scan trajectory scheduling is performed when the group of elements with the wide directivity angle is selected. Reference numeral G1 represents a high-resolution region formed by the group of elements with the wide directivity angle. The circle (solid line) represents the region of interest R1 set by the user, which is the cross-sectional diagram taken along an X-Y scanning plane. Here, the scanning region setting unit 800 determines the spiral pitch and photoacoustic measurement positions in such a manner that the high-resolution regions G1 fill the region of interest R1. In this case, the spiral pitch is determined based on the diameter of each high-resolution region G1. In order to fill the region of interest R1 with the high-resolution regions G1, the spiral pitch needs to be equal to or less than the diameter of the high-resolution regions G1. In the present embodiment, the spiral pitch is equal to the diameter of the high-resolution regions G1.

In this case, the spiral trajectory based on the spiral pitch calculated in the foregoing manner is formed in to substantially a concentric circle in the region of interest R1, as shown in FIG. 4A. Consequently, the number of windings of the spiral is determined. In the present embodiment, the number of windings of the spiral is obtained by dividing the radius of the region of interest R1 by the spiral pitch. Furthermore, as shown in FIG. 4A, spreading the high-resolution regions G1 all over the spiral trajectory enables determination of the photoacoustic measurement positions on the spiral trajectory. At this moment, the scan speed can also be determined based on the photoacoustic measurement positions and the emission cycle of the light source 100.

Light emission and acoustic wave detection may be executed at the positions where the supporting member stops, while the supporting member stops and moves repeatedly, or may be executed while the supporting member moves continuously.

Figure 4B:
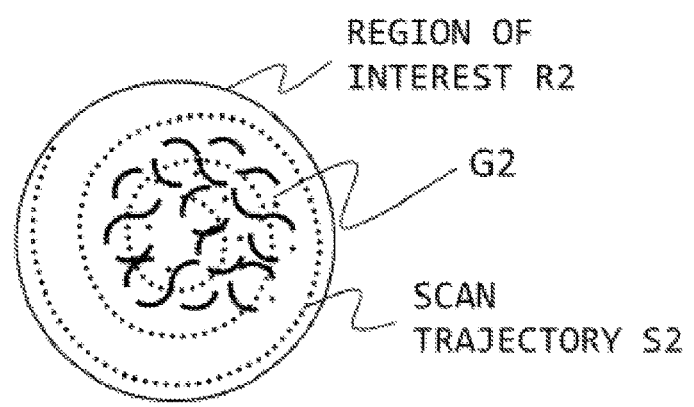

FIG. 4B shows how the scan trajectory scheduling is performed when the group of elements with the narrow directivity angle is selected. As with the scheduling method described with reference to FIG. 4A, the scan trajectory and the scan speed can be determined. In case of FIG. 4B, a narrow region is measured at high sensitivity based on the contents input by the user.

The scanner 900 scans the supporting member 400 in accordance with the scan trajectory determined in the foregoing procedure. Photoacoustic measurement is executed as follows at each of the scanned positions (step S5).

First, light is emitted from the light source 100 to the first position on the scan trajectory (the first measurement position), and the object E is irradiated by the optical system 200 through the acoustic matching material 1000. Consequently, the light radiated on the object E is absorbed by the object E, generating photoacoustic waves. The photoacoustic waves generated in the object E are transmitted to and received by the acoustic detection elements 300 through the acoustic matching material 1000 and converted into electric signals.

Of the resultant electric signals, only the signal of the element selected by the element selecting unit 500 is sent to the signal processing unit 600, associated with the information on the first measurement information, and stored as a first electric signal for the first measurement position in the storage device such as a memory. At this moment, the electric signals from all the elements with the wide and narrow directivity angles may be obtained, and then an electric signal may be selected based on the conditions. Alternatively, only an electric signal from the element having the selected directivity angle may be acquired by means of a switching process or the like that is performed in advance. This is the same as saving the electric signal that is output from a detection element of the selected pattern. It is not necessary to store the electric signal that is output from a detection element that is not included in the selected pattern.

Next, the scanner 900 moves the supporting member 400 to a second measurement position located within the movement region set by the scanning region setting unit 800. With the same step as the step of measuring the first measurement position, a second electric signal for the second measurement position is acquired.

Subsequently, as with the foregoing step, electric signals of all the measurement positions within the movement region set by the scanning region setting unit 800 are acquired.

The signal processing unit 600 generates an image of the region of interest in the object by using the electric signal acquired for each measurement position (step S6).

Through the use of the apparatus configured as described above, the high-resolution region and the scan trajectory can be adjusted based on the measurement instruction input by the user (the measurement mode in particular). Accordingly, favorable scheduling can be realized with less elements that require a lengthy time. As a result, photoacoustic imaging that addresses the user needs can be realized based on the measurement conditions such as resolution in measurement and the width of a measurement region.

The present embodiment has described two types of measurement techniques: quick scan and detailed scan. In fact, however, there may be more scan modes to be implemented. For example, as one of the measurement conditions, a mode for scanning with a medium resolution in a reasonable amount of time may be set.

Resolution is used the index for the quality of data to be obtained in the present embodiment; however, the scan modes may be defined by focusing on the parameters such as contrast that affect the image quality of a reconstructed image. In addition, selecting an element to be used based on the scan mode is merely an example; thus, the element to be used may actually be determined based on another index. For instance, an element to be used may be selected using a method for referring to the abovementioned resolutions and contrasts as target values or a method for using the size or width of a designated three-dimensional region of interest or the time it takes for measurement as the indices.

A method for designating the target values of the resolutions and contrasts in five stages may be used. In this case, target value designation can be implemented when the apparatus is provided with a data list in which combinations of elements satisfying the target values are shown as preset values and a control program determines an element to be used by reference to the table in accordance with the target values. In to the method for designating a resolution, the user can prioritize the resolutions and instruct forming a reconstructed image in which small changes in the optical absorption properties are focused. In the method for designating a contrast, it is possible to instruct forming a reconstructed image that focuses on the contrast properties, and this enables acquisition of an image overlooking the distribution of the optical absorption properties. Because resolutions and contrasts contradict with each other, it is crucial to achieve a balance therebetween. With setting of targets being enabled for the parameters as described above, finer image quality adjustment can be implemented in an optical absorption distribution image.

Moreover, according to the present embodiment, the acoustic detection elements with two types of directivity properties are disposed in the apparatus; however, acoustic detection elements having more types of directivity properties may be employed. The present embodiment has introduced a method for selecting an acoustic detection element to be used for measurement, for each group having directivity properties; however, a method for using a combination of acoustic detection elements having various directivities may be employed.

Embodiment 2

The present embodiment describes a method for changing the shape of the high-resolution region. In the present embodiment as well, a photoacoustic apparatus having the same configuration as that described in Embodiment 1 can be employed.

Figure 5:
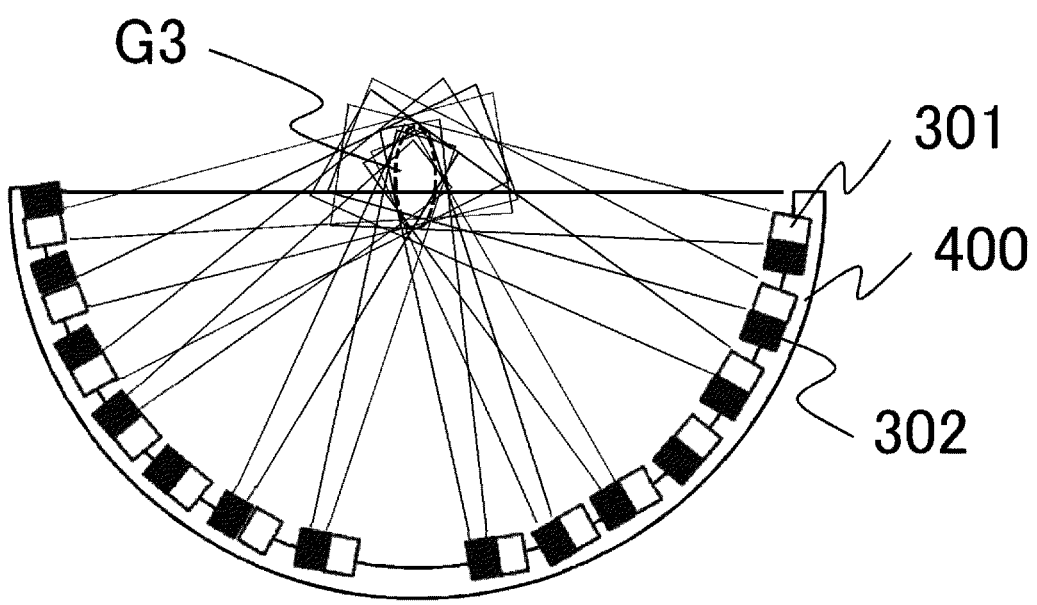
FIG. 5 is an explanatory diagram of a high-resolution region according to Embodiment 2.

As shown in FIG. 5, the shape of the high-resolution region can be changed by using the acoustic detection elements 301 with the wide directivity angle and the acoustic detection elements 302 with the narrow directivity angle. The overview of FIG. 5 basically has the same details as FIG. 3, in which the white acoustic detection elements represent the acoustic detection elements 301 with the wide directivity angle and the black acoustic detection elements represent the acoustic detection elements 302 with the narrow directivity angle. The lines extending radially from the acoustic detection elements represent the ranges within the directivity angles of the elements. A dotted line circle G3 shown in the diagram represents a high-resolution region that is obtained when the elements with the radial lines in the diagram are selected as the acoustic detection elements to be used for measurement.

As shown in FIG. 5, the shape of the high-resolution region can be changed to a vertically long spherical shape or an almond shape by using the acoustic detection elements with the narrow directivity angle in the vicinity of the bottom surface of the supporting member 400 and selecting the acoustic detection elements with the wide directivity angle around the rim of the supporting member. In this manner, not only a vertically long shape but also any desired shape of a high-resolution region can be obtained.

By forming a vertically long, spherical high-resolution region that extends in the Z-axis direction as shown in FIG. 5, favorable measurement can be executed even when an region of interest extending in the direction of the Z-axis is set by the user.

By forming the high-resolution region only with the wide directivity angle group, it becomes possible to implement measurement of a large high-resolution region, however, the overall sensitivity thereof is likely to drop. On the other hand, with the method shown in FIG. 5, the elements with the narrow directivity angle can be used as well. This prevents a decrease in the sensitivity while expanding the high-resolution region. Particularly, such a beneficial effect can be exhibited even more prominently as the aspect ratio of the region of interest increases in the direction of the Z axis or the diameter of the spherical high-resolution region is greater than the diameter of the conventional spherical high-resolution region.

Following is an additional explanation of the measurement sequence according to the present embodiment. Although the measurement sequence is basically the same as that of Embodiment 1, implementation of the functions associated with the following sequence is possible in view of the fact that the shape of the high-resolution region can be changed.

(When the User Inputs an Instruction on the Shape of the High-Resolution Region)

The apparatus has shape patterns of the high-resolution region (reference patterns) as the preset values. Using the inputting unit 700, the user designates which one of the shape patterns to use. For example, a desired pattern can be selected from a plurality of patterns displayed on the display unit. The element selecting unit 500 has a reference table for determining which element combination to select for each shape pattern of the high-resolution region. The element selecting unit 500 therefore determines the elements to be used with reference to the table in accordance with the shape pattern selected by the user. Each of the patterns may be configured by a combination of elements of at least two or more properties.

The subsequent processes are the same as those described in Embodiment 1. In other words, scanning scheduling is performed by the scanning region setting unit 800 based on the shape of the three-dimensional region of interest and the shape of the high-resolution region, and photoacoustic measurement is performed, to reconstruct the image of the inside of the object.

As a result, the user can designate measurement of the suitable high-resolution region in accordance with the shape of the region of interest set by the user.

(When Automatically Matching the Shape of the High-Resolution Region with the Shape of the Region of Interest)

A function for automatically changing the shape of the high-resolution region in accordance with the shape of the three-dimensional region of interest designated by the user can be considered as another implementation method. As an example of the function, a system that focuses on the shape of the three-dimensional region of interest designated by the user to change the combination of elements to be used at the aspect ratio of the region of interest is described next.

Once the measurement conditions are input, the element selecting unit 500 obtains the aspect ratio of the three-dimensional region of interest designated by the user. For example, when a flat shape that is squished in the Z-axis direction is instructed, the element selecting unit 500 selects a combination of elements that leads to the formation of an elliptical high-resolution region having the long axis extending in the Z-axis direction. In the present embodiment, the method for determining a combination of elements for each shape is a method for selecting any of the preset values that are stored in the memory as the information on the combinations of elements for realizing several types of shapes.

The subsequent processes are the same as those described in Embodiment 1, in which scanning scheduling is executed by the scanning region setting unit 800 based on the shape of the three-dimensional region of interest and the shape of the high-resolution region, whereby the measurements can be implemented.

When the user can designate the measurement time, target resolution, target contrast or the like as a detailed measurement parameter, the element selecting unit 500 can select a combination of elements that can satisfy these measurement conditions. Therefore, an apparatus that automatically executes measurement in view of the detailed parameters without specifically making the user conscious of the shape of the high-resolution region can be provided.

According to the present embodiment, setting of a high-resolution region and scanning scheduling can be executed in accordance with the measurement conditions input by the user. As a result, photoacoustic imaging that accommodates the needs of the user can be realized in accordance with resolution in measurement and the size of the measurement region, realizing photoacoustic measurement that is favorable to the user and the subject person.

In each of the foregoing embodiments, the detection elements are divided into groups beforehand in accordance with the element properties, and the user selects the shape of the region of interest and a group, thereby determining the shape of the high-resolution region. However, after the user inputs the shape of the region of interest or the shape of the high-resolution region, the elements that are suitable for these shapes can be picked up depending on the properties (directivity or sensitivity) of each element or the position of each element.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-131663, filed on Jun. 26, 2014, which is hereby incorporated by reference herein in its entirety.

What is claimed is:

1. An object information acquiring apparatus comprising:
a light source;
a detector array including a plurality of detection elements configured to detect acoustic waves generated as a result of irradiation of light from the light source onto an object and to output electric signals and a supporting member configured to support the plurality of detection elements in a certain arrangement so that axes of directivity of at least a part of the plurality of detection elements gather;
an inputting unit configured to receive an input of a measurement condition from a user;
a selecting unit configured to select at least a part of the plurality of detection elements; and
a processing unit configured to acquire property information on the inside of the object, using electric signals output from the detection elements selected by the selecting unit,
wherein the plurality of detection elements includes at least two groups of detection elements, the groups being different in a directivity angle,
wherein the selecting unit selects at least one group of detection elements based on the measurement condition input by the user,
wherein the at least two groups of detection elements includes a first group of detection elements and a second group of detection elements, and the detection elements of the first group have a wider directivity angle than the detection elements of the second group,
wherein the inputting unit indicates to the user at least two types of measurement modes including a quick scan mode and a detailed scan mode to be able to be specified by the user,
wherein the selecting unit selects at least the first group of detection elements in case the quick scan mode is specified by the user, and
wherein the selecting unit selects at least the second group of detection elements in case the detailed scan mode is specified by the user.

2. The object information acquiring apparatus according to claim 1, wherein the selecting unit selects only the first detection elements or only the second detection elements in accordance with the measurement condition input by the user.

3. The object information acquiring apparatus according to claim 1, further comprising:
a scanning unit configured to move the supporting member,
wherein the inputting unit is configured to receive an input of a first measurement condition under which a pitch between positions of the supporting member obtained at each light irradiation is a predetermined value, and an input of a second measurement condition under which the pitch is a value smaller than the predetermined value, and
the selecting unit selects only the first detection elements when the first measurement condition is input by the inputting unit and selects only the second detection elements when the second measurement condition is input by the inputting unit.

4. The object information acquiring apparatus according to claim 1, further comprising:
a scanning unit configured to move the detector array,
wherein the inputting unit is configured to have input a scanning manner for scanning the detector array by the scanning unit as the measurement condition, and
the selecting unit selects at least a part of the plurality of detection elements in accordance with the scanning manner.

5. The object information acquiring apparatus according to claim 1, further comprising a scanning unit that moves the supporting member,
wherein the scanning unit moves the supporting member on a scan trajectory based on a high-resolution region that is formed by the detection elements selected by the selecting unit.

6. The object information acquiring apparatus according to claim 5, wherein the high-resolution region is a region where the property information can be acquired at a predetermined resolution or higher.

7. The object information acquiring apparatus according to claim 1, wherein the processing unit stores the electric signals that are output from the detection elements selected by the selecting unit.

8. The object information acquiring apparatus according to claim 1, wherein the processing unit does not store electric signals that are output from detection elements that are not selected by the selecting unit.

9. The object information acquiring apparatus according to claim 1, wherein the inputting unit is configured to receive the measurement condition including at least one of a designation of a region of interest where the property information is acquired, and a resolution of the property information in the region of interest, and the amount of time required to acquire the property information from the region of interest.

10. The object information acquiring apparatus according to claim 1, wherein the directivity angles of the detection elements vary by patterns.

11. The object information acquiring apparatus according to claim 1, wherein the plurality of detection elements are arranged along a surface having curvature of a part of a sphere or an ellipsoid.

12. The object information acquiring apparatus according to claim 1, further comprising a display unit configured to display an image of the inside of the object based on the property information.

13. The object information acquiring apparatus according to claim 1, further comprising a display unit configured to indicate a plurality of measuring modes to be specified by the user,
wherein the inputting unit indicates at least two types of measurement modes on the display unit.

14. An object information acquiring method comprising:
a first step of determining a measurement condition;
a second step of selecting at least a part of a plurality of detection elements in a certain arrangement configured to output electric signals corresponding to acoustic waves generated as a result of irradiation of light onto an object, and disposed in a manner that axes of directivity gather; and
a third step of acquiring property information on the inside of the object by using the electric signals output from the detection elements selected in the second step,
wherein the plurality of detection elements includes at least two groups of detection elements, the groups being different in a directivity angle,
wherein at least one group of detection elements is selected in the second step based on the measurement condition determined in the first step,
wherein the at least two groups of detection elements includes a first group of detection elements and a second group of detection elements, and the detection elements of the first group have a wider directivity angle than the detection elements of the second group,
wherein at least two types of measurement modes including a quick scan mode and a detailed scan mode are able to be specified as the measurement condition determined in the first step,
wherein at least the first group of detection elements is selected in the second step in case the quick scan mode is specified as the measurement condition, and
wherein at least the second group of detection elements is selected in the second step in case the detailed scan mode is specified as the measurement condition.

15. An object information acquiring apparatus comprising:
a light source;
a detector array including a first group of detection elements configured to detect acoustic waves from an object in a quick scan mode and a second group of detection elements configured to detect acoustic waves from an object in a detailed scan mode;
an inputting unit configured to indicate at least two types of measurement modes including a quick scan mode and a detailed scan mode to be specified by an input from the user;
a selecting unit configured to select at least a part of the detection elements in the detector array; and
a processing unit configured to acquire property information on the inside of the object, using electric signals output from the detection elements selected by the selecting unit,
wherein the selecting unit selects at least the first group of detection elements in case the quick scan mode is specified by the user,
wherein the selecting unit selects at least the second group of detection elements in case the detailed scan mode is specified by the user, and
wherein the detection elements of the first group have a wider different directivity angle than the detection elements of the second group.

16. The object information acquiring apparatus according to claim 15, further comprising a scanning unit that moves the first group of detection elements and the second group of detection elements integrally.

17. The object information acquiring apparatus according to claim 15, further comprising a supporting member configured to support the first group of detection elements and the second group of detection elements and to be moved by the scanning unit.

18. The object information acquiring apparatus according to claim 15, wherein axes of directivity of at least a part of the first group of detection elements and axes of directivity of at least a part of the second group of detection elements gather in a concentric manner.

19. An object information acquiring method comprising:
a first step of determining a measurement condition configured to set a scanning mode to the object information acquiring apparatus including a first group of detection elements adapted for a quick scan mode and a second group of detection elements adapted for a detailed scan mode;
a second step of selecting at least a part of a plurality of the detection elements configured to detect acoustic waves from an object, the acoustic waves generated as a result of irradiation of light onto the object; and
a third step of acquiring property information of the object by using electric signals output from the detection elements selected in the second step,
wherein the first step is performed configured to indicate at least two types of measurement modes including the quick scan mode and the detailed scan mode to be specified by an input from the user,
wherein the second step is performed configured to select at least the first group of detection elements in case the quick scan mode is specified in the first step, and
wherein the second step is performed configured to select at least the second group of detection elements in case the detailed scan mode is specified in the first step, and
wherein the detection elements of the first group have a wider different directivity angle than the detection element of the second group.

20. The object information acquiring method according to claim 19, wherein the third step is performed in the scanning mode specified in the first step, while the detection elements selected in the second step are moved with respect to the object and detect the acoustic waves from the object.

21. The object information acquiring method according to claim 19, wherein axes of directivity of at least a part of the first group of detection elements and axes of directivity of at least a part of the second group of detection elements gather in a concentric manner.

* * * * *